(12) United States Patent
Sauve et al.

(10) Patent No.: US 11,028,118 B2
(45) Date of Patent: *Jun. 8, 2021

(54) EFFICIENT SYNTHESIS OF NICOTINAMIDE MONONUCLEOTIDE

(71) Applicant: Cornell University, Ithaca, NY (US)

(72) Inventors: Anthony Sauve, New Rochelle, NY (US); Farheen Sultana Yang Mohammed, Jackson Heights, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/820,548

(22) Filed: Mar. 16, 2020

(65) Prior Publication Data

US 2020/0216487 A1 Jul. 9, 2020

Related U.S. Application Data (63) Continuation of application No. 15/562,336, filed as application No. PCT/US2016/024054 on Mar. 24, 2016, now Pat. No. 10,590,160.

(60) Provisional application No. 62/139,235, filed on Mar. 27, 2015, provisional application No. 62/155,920, filed on May 1, 2015.

(51) Int. Cl.
  *C07H 19/048* (2006.01)
  *C07H 1/02* (2006.01)

(52) U.S. Cl.
  CPC ............. *C07H 19/048* (2013.01); *C07H 1/02* (2013.01)

(58) Field of Classification Search
  CPC .............................. C07H 1/02; C07H 19/048
  See application file for complete search history.

(56) References Cited

U.S. PATENT DOCUMENTS

| | | | |
|---|---|---|---|
| 3,201,389 A * | 8/1965 | Fujimoto | C07H 1/02 536/26.21 |
| 3,451,997 A | 6/1969 | Fujimoto et al. | |
| 4,894,388 A | 1/1990 | Fleet | |
| 5,879,700 A | 3/1999 | Hosteller | |
| 10,590,160 B2 * | 3/2020 | Sauve | C07H 19/048 |

OTHER PUBLICATIONS

Araki, et al., "Increased Nuclear NAD Biosynthesis and SIRT1 Activation Prevent Axonal Degeneration", *Science*, 305: 1010-1013 (2004).
Berge et al., "Pharmaceutical Salts", *Journal of Pharmaceutical Sciences*, 66(1): 1-19 (1977).
Berger, et al., "Regulation of poly(ADP-ribose) polymerase 1 activity by the phosphorylation state of the nuclear NAD biosynthetic enzyme NMN adenylyl transferase 1", *Proc. Natl. Acad. Sci. U.S.A.*, 104(10): 3765-3770 (2007).
Blasco, "Telomeres and Human Disease: Ageing, Cancer and Beyond", *Nature Reviews Genetics*, 6: 611-622 (2005).
Bruzzone, et al., "Cyclic ADP-ribose is a second messenger in the lipopolysaccharide-stimulated proliferation of human peripheral blood mononuclear cells", *Biochem. J.*, 375: 395-403 (2003).
Burgos, et al., "Weak Coupling of ATP Hydrolysis to the Chemical Equilibrium of Human Nicotinamide Phosphoribosyltransferase†", *Biochemistry*, 47: 11086-11096 (2008).
Culver, et al., "A 2'-Phosphotransferase Implicated in tRNA Splicing Is Essential in *Saccharomyces cerevisiae**", *Journal of Biological Chemistry*, 272(20): 13203-13210 (1997).
Di Girolamo, et al., "K-ras Transformation Greatly Increases the Toxin-dependent ADP-ribosylation of GTP Binding Proteins in Thyroid Cells", *The Journal of Biological Chemistry*, 267(24): 17397-17403 (1992).
Guarente, et al., "Calorie Restriction—the SIR2 Connection", *Cell*, 120: 473-482 (2005).
Guse, et al., "A Minimal Structural Analogue of Cyclic ADP-ribose", *The Journal of Biological Chemistry*, 280(16): 15952-15959 (2005).
Jarman et al., "4-Substituted Nicotinic Acids and Nicotinamides. Part II. The Preparation of 4-Methylnicotinamide Riboside", *Journal of Chemical Society* (C), 2:199-203 (1969).
Jeck, et al., "Simple Methods for Preparing Nicotinamide Mononucleotide and Related Analogs", *Vitamins and Coenzymes, Methods in Enzymology*, 66: 62-70 (1980).
Magni, et al., "Enzymology of NAD+ homeostasis in man", *Cell. Mol. Life Sci.*, 61: 19-34 (2004).
Marmorstein, "Structure and chemistry of the Sir2 family of NAD+-dependent histone/protein deactylases", *Biochemical Society Transactions*, 32: 904-909 (2004).
Meyer et al., "NAD (S), an NAD analogue with reduced susceptibility to phosphodiesterase. Chemical synthesis and enzymatic properties", *European Journal of Biochemistry*, 140(3): 531-537 (1984).
Michan, et al., "Sirtuins in mammals: insights into their biological function", *Biochem. J.*, 404(1): 1-13 (2007).
Nakano, et al., "Purification and molecular cloning of a DNA ADP-ribosylating protein, CARP-1, from the edible clam *Meretrix lamarckii*", *Proc. Natl. Acad. Sci. U.S.A.*, 103(37): 13652-13657 (2006).

(Continued)

*Primary Examiner* — Lawrence E Crane
(74) *Attorney, Agent, or Firm* — Leydig, Voit & Mayer, Ltd.

(57) ABSTRACT

The invention provides a process for the preparation of nicotinamide mononucleotide having formula (I):

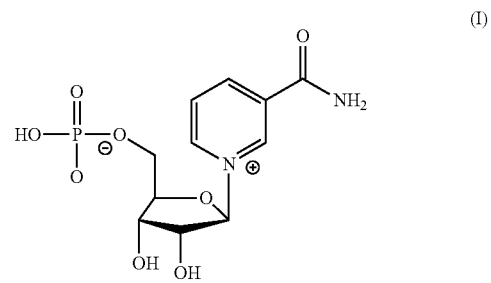

The method involves the protection of nicotinamide riboside by ketalization, followed by phosphorylation and then deprotection to provide nicotinamide mononucleotide.

5 Claims, 4 Drawing Sheets

(56) References Cited

OTHER PUBLICATIONS

Petit et al., "Oxidation of pyridine nucleotides during Fas- and ceramide-induced apoptosis in Jurkat cells: correlation with changes in mitochondria, glutathione depletion, intracellular acidification and caspase 3 activation", *Biochem. J.*, 353: 357-367 (2001).
Pollak, et al, "The power to reduce: pyridine nucleotides—small molecules with a multitude of functions", *Biochem. J.*, 402: 205-218 (2007).
Remington's Pharmaceutical Sciences, 18th ed., Mack Publishing Company, Easton, PA, 1990, p. 1445.
Rozenberg, et al., "Theoretical Studies of the Quinolinic Acid to Nicotinic Acid Mononucleotide Transformation", *J. Org. Chem.*, 73: 9314-9319 (2008).
Sauve, et al., "Sir2 Regulation by Nicotinamide Results from Switching between Base Exchange and Deacetylation Chemistry\", *Biochemistry*, 42(31): 9249-9256 (2003).
Seman, et al., "NAD-Induced T Cell Death: ADP-Ribosylation of Cell Surface Proteins by ART2 Activates the Cytolytic P2X7 Purinoceptor", *Immunity*, 19: 571-582 (2003).
Song, et al., "Extracellular NAD is a regulator for $Fc^{\gamma}R$-mediated phagocytosis in murine macrophages", *Biochemical and Biophysical Research Communications*, 367: 156-161 (2008).
Suhadolnik, et al., "Role of Adenine Ring and Adenine Ribose of Nicotinamide Adenine Dinucleotide in Binding and Catalysis with Alcohol, Lactate, Glyceraldehyde-3-phosphate Dehydrogenases", *The Journal Biological Chemistry*, 252(12): 4125-4133 (1977).
Yang, et al., "Syntheses of Nicotinamide Riboside and Derivatives: Effective Agents for Increasing Nicotinamide Adenine Dinucleotide Concentrations in Mammalian Cells", *J. Med. Chem.*, 50: 6458-6461 (2007).
Ziegler, M., "New functions of a long-known molecule: Emerging roles of NAD in cellular signaling", *Eur. J. Biochem.*, 267: 1550-1564 (2000).
WIPO, International Search Report in International Application PCT/US16/24054 dated Jun. 10, 2016 (3 pages).
European Patent Office, extended European Search Report in Application No. 16773806.1 dated Dec. 19, 2017, 15 pages.

\* cited by examiner

EFFICIENT SYNTHESIS OF NICOTINAMIDE MONONUCLEOTIDE

CROSS-REFERENCE TO RELATED APPLICATIONS

This patent application is a continuation of U.S. patent application Ser. No. 15/562,336, filed Sep. 27, 2017, which is the U.S. national phase of International Patent Application No. PCT/US2016/024054, filed Mar. 24, 2016, which claims the benefit of U.S. Provisional Patent Application No. 62/139,235, filed Mar. 27, 2015, and 62/115,920, filed May 1, 2015, which are incorporated by reference for all purposes.

FEDERALLY SPONSORED RESEARCH AND DEVELOPMENT

This invention was made with government support under GM106072 awarded by the National Institutes of Health. The government has certain rights in the invention.

BACKGROUND OF THE INVENTION

The cellular redox reactions of coenzymes $NAD^+$, NADH and $NADP^+$, NADPH are well known (Pollak, N. et al, Biochem. J., 402: 205-218 (2007)). It is known that $NAD^+$ plays an important role in apoptosis (Gendron, M. C. et al., Biochem. J., 353: 357 (2001)), calcium mobilization (Guse, A. H. et al., J. Biol. Chem., 280: 15952 (2005)), cell proliferation (Bruzzone, S. et al., Biochem. J., 375: 395 (2003)), aging (Blasco, M. A., Nat. Rev. Genet., 6: 611 (2005)), gene expression (Girolamo, M. D. et al., J Biol. Chem., 282: 16441 (2007); Sauve, A. A.; Schramm, V. L., Biochemistry, 42: 9249 (2003); Michan, S. et al., Biochem. J., 404: 1 (2007); Nakano, T. et al., Proc. Natl. Acad. Sci. U.S.A., 103: 13652 (2006); Culver, G. M. et al., J. Biol. Chem., 272: 13203 (1997); Berger, F. et al., Proc. Natl. Acad. Sci. USA., 104: 3765 (2007)), immune system modulation (Song, E. K. et al., Biochem. Biophys. Res. Commun., 367: 156 (2008); Seman, M. et al., Immunity, 19: 571 (2003)), energy metabolism and metabolic regulation. Mono and poly (ADP-ribose) polymerases use $NAD^+$ as substrate for protein covalent modifications (Ziegler, M., Eur. J. Biochem., 267: 1550 (2000); Guarente, L. et al., Cell, 120: 473 (2005); Marmorstein, R., Biochem. Soc. Trans., 32: 904 (2004); Magni, G. et al., Cell. Mol. Life Sci., 61: 19 (2004); Araki, T. et al., Science, 305: 1010 (2004)). $NAD^+$ can be synthesized enzymatically (Suhadolnik, R. J. et al., Biol. Chem., 252: 4125 (1977)) and chemically (Jeck, R. et al., Eds., Academic: New York, 66: 62 (1979)) from various precursors of vitamin $B_3$ (nicotinic acid (NA), nicotinamide (Nam), nicotinamide riboside (NR), nicotinamide mononucleotide (NMN)) and from tryptophan. $NAD^+$-utilizing reactions liberate nicotinamide, which is recycled to form NMN from nicotinamide and 5-phosphoribosyl pyrophosphate using the enzyme nicotinamide phosphoribosyltransferase. The synthesized NMN reacts with ATP and is converted to $NAD^+$ by nicotinamide mononucleotide adenyltransferase (NMNAT).

Increasing interest in precursors that can be administrated to increase physiological $NAD^+$ provides impetus to develop efficient and practical syntheses of precursors such as NR and NMN. A highly efficient chemical synthesis of NR has been developed (Yang, T. et al., J. Med. Chem., 50: 6458 (2007)). Literature indicates that aside from enzymatic reactions there are few different chemical methods for the synthesis of nicotinamide mononucleotide and derivatives (Burgos, E. S. et al., Biochemistry, 47: 11086 (2008); Rozenberg, A. et al., J. Org. Chem., 73: 9314 (2008)). Existing synthetic strategies involve complicated intermediates, and isolation of NMN is difficult in good yields. Moreover, enzymatic reactions are typically limited to small scale chemical synthesis and are expensive, and thus are less immediately scalable to multigram or kilogram scale.

Thus, there is an unmet need for an improved process for the preparation of nicotinamide mononucleotide.

BRIEF SUMMARY OF THE INVENTION

The invention provides a process for the preparation of nicotinamide mononucleotide having formula (I):

or a salt thereof, wherein the process comprises the steps of:
(i) reacting nicotinamide riboside having formula (II):

with a ketalization reagent that is $R^1R^2C(OR^3)(OR^4)$ or $R^1R^2C=O$,
wherein $R^1$ and $R^2$ are independently $C_1$-$C_6$ alkyl or, taken together along with the carbon atom to which they are attached, form a 5-7 membered carbocyclic or heterocyclic ring, and wherein $R^3$ and $R^4$ are independently $C_1$-$C_6$ alkyl, in a solvent in the presence of an acid catalyst, to form a compound of formula (III):

(ii) isolating the compound of formula (III),
(iii) reacting the compound of formula (III) with a mixture of POCl$_3$ and PO(OR$^5$)$_3$, wherein R$^5$ is C$_1$-C$_6$ alkyl, followed by treatment with water to form a compound of formula (IV):

(iv) isolating the compound of formula (IV),
(v) reacting the compound of formula (IV) with an acid catalyst in a solvent or mixture of solvents to provide nicotinamide mononucleotide, and
(vi) isolating nicotinamide mononucleotide.

The invention also provides a process for the preparation of a compound of formula (III):

(III)

wherein R$^1$ and R$^2$ are independently C$_1$-C$_6$ alkyl or, taken together along with the carbon atom to which they are attached, form a 5-7 membered carbocyclic or heterocyclic ring, wherein the process comprises the step of reacting nicotinamide riboside of formula (II):

with a ketalization reagent that is R$^1$R$^2$C(OR$^3$)(OR$^4$) or R$^1$R$^2$C=O,
wherein R$^1$ and R$^2$ are independently C$_1$-C$_6$ alkyl or, taken together along with the carbon atom to which they are attached, form a 5-7 membered carbocyclic or heterocyclic ring, and wherein R$^3$ and R$^4$ are independently C$_1$-C$_6$ alkyl, in a solvent in the presence of an acid catalyst, to form the compound of formula (III).

The invention further provides a process for the preparation of a compound of formula (IV):

or a salt thereof, wherein R$^1$ and R$^2$ are independently C$_1$-C$_6$ alkyl or, taken together along with the carbon atom to which they are attached, form a 5-7 membered carbocyclic or heterocyclic ring,
wherein the process comprises the step of reacting a compound of formula (III):

with a mixture of POCl$_3$ and PO(OR$^5$)$_3$, wherein R$^5$ is C$_1$-C$_6$ alkyl, followed by treatment with water to form a compound of formula (IV).

The invention additionally provides a process for the preparation of nicotinamide mononucleotide having formula (I):

or a salt thereof, wherein the process comprises the step of reacting a compound of formula (IV):

wherein R¹ and R² are independently $C_1$-$C_6$ alkyl or, taken together along with the carbon atom to which they are attached, form a 5-7 membered carbocyclic or heterocyclic ring, with an acid catalyst in a solvent or mixture of solvents to provide nicotinamide mononucleotide.

DETAILED DESCRIPTION OF THE INVENTION

The invention provides a process for the preparation of nicotinamide mononucleotide having formula (I):

or a salt thereof, wherein the process comprises the steps of:
reacting nicotinamide riboside having formula (II):

with a ketalization reagent that is R¹R²C(OR³)(OR⁴) or R¹R²C=O,
wherein R¹ and R² are independently $C_1$-$C_6$ alkyl or, taken together along with the carbon atom to which they are attached, form a 5-7 membered carbocyclic or heterocyclic ring, and wherein R³ and R⁴ are independently $C_1$-$C_6$ alkyl, in a solvent in the presence of an acid catalyst, to form a compound of formula (III):

(ii) isolating the compound of formula (III),
(iii) reacting the compound of formula (III) with a mixture of $POCl_3$ and $PO(OR^5)_3$,
wherein R⁵ is $C_1$-$C_6$ alkyl, followed by treatment with water to form a compound of formula (IV):

(iv) isolating the compound of formula (IV),
(v) reacting the compound of formula (IV) with an acid catalyst in a solvent or mixture of solvents to provide nicotinamide mononucleotide, and
(vi) isolating nicotinamide mononucleotide.

In an embodiment, nicotinamide mononucleotide is synthesized as shown in Scheme 1.

Nicotinamide riboside 1, wherein X⁻ is an anion, is reacted with a ketalization reagent that is $R^1R^2C(OR^3)(OR^4)$ or $R^1R^2C=O$, wherein $R^1$ and $R^2$ are independently $C_1$-$C_6$ alkyl or, taken together along with the carbon atom to which they are attached, form a 5-7 membered carbocyclic or heterocyclic ring, and wherein $R^3$ and $R^4$ are independently $C_1$-$C_6$ alkyl, in a solvent in the presence of an acid catalyst, to form compound 5. In a preferred embodiment, the ketalization reagent is $R^1R^2C(OR^3)(OR^4)$ and more preferably is 2,2-dimethoxypropane.

It will be understood that, when a compound is shown as a cation without having an anion, the positive charge on the cation can be countered by any suitable anion or anionic component having a negative charge. The anion can be any suitable organic, inorganic, or polymeric anion without limitation. In an embodiment, the anion is trifluoromethanesulfonate.

The acid catalyst can be any suitable acid catalyst, for example, the acid catalyst can be an inorganic acid catalyst such as sulfuric acid, hydrochloric acid, phosphoric acid, and the like. The acid catalyst can be an organic acid catalyst, for example, p-toluenesulfonic acid, methylsulfonic acid, trifluoromethylsulfonic acid, and the like. In a preferred embodiment, the acid catalyst is sulfuric acid, more preferably concentrated sulfuric acid.

The solvent can be any suitable solvent and can be, for example, acetonitrile, dichloromethane, acetone, dimethylformamide, dimethylsulfoxide, and the like. Preferably, the solvent is acetonitrile.

The ketalization can be conducted at any temperature. For example, the ketalization can be conducted at about 0° C. to about 50° C. Preferably, the ketalization is conducted starting at about 0° C. followed by warming to room temperature.

Compound 5 can be optionally isolated by quenching the reaction mixture with a base such as sodium carbonate, followed by filtration and then evaporation of solvents. In other embodiments, the reaction mixture can be partitioned between water and an organic solvent such as dichloromethane, ethyl acetate, and the like. The acid catalyst can be neutralized before partitioning or can be quenched in an aqueous solution of a base followed by extraction with a solvent. Compound 5 can be isolated by silica gel chromatography or by crystallization.

Compound 5 can be phosphorylated using any suitable conditions, for example, compound 5 can be phosphorylated in a mixture of phosphorus oxychloride and $PO(OR^5)_3$, wherein $R^5$ is $C_1$-$C_6$ alkyl. Preferably, compound 5 is phosphorylated in a mixture of phosphorus oxychloride and triethylphosphate to provide compound 6. The phosphorylation can be conducted at any suitable temperature. For example, the phosphorylation can be conducted at about 0° C. to about 50° C. and is preferably conducted at 0° C.

Compound 6 can be optionally isolated by quenching the reaction mixture with a base such as sodium carbonate, followed by extraction of excess unreacted triethylphosphate with a solvent such as ethyl acetate and then recovery of compound 6 from the aqueous layer by evaporation. Compound 6 can be isolated by silica gel chromatography or by crystallization.

Nicotinamide mononucleotide 4 is obtained by deprotection of compound 6 via acid catalyzed deketalization. The deprotection can be conducted in an aqueous solvent mixture, for example, in a mixture of dichloromethane and water. The deprotection can be conducted in a nonaqueous solvent. For example, the deprotection can be conducted in a hydroxylic solvent such as methanol or ethanol, preferably in methanol. The acid catalyst can be any suitable acid catalyst as described herein in connection with the preparation of compound 5, and is preferably trifluoromethanesulfonic acid or concentrated hydrochloric acid.

Nicotinamide mononucleotide can be isolated using any suitable isolation procedure. For example, the reaction mixture can be at least partially evaporated to remove volatile organic solvent, and the residue can be treated with water and then neutralized to pH 5-6 with a base such as sodium carbonate. The crude product can be purified in any suitable manner to provide purified nicotinamide mononucleotide. For example, the crude product can be purified using reverse phase chromatography on a C18 column with water as eluent to provide purified nicotinamide mononucleotide.

Nicotinamide mononucleotide of formula (I) and the compound of formula (IV) can be in the form of a zwitterion or any suitable salt thereof. For example, nicotinamide mononucleotide of formula (I) and the compound of formula (IV) can be in the form of a protonated salt or a monobasic salt thereof. As used herein, the term protonated salt refers to the compounds of formulas (I) and (IV) wherein the phosphate (—O—P(=O)(OH)$_2$ group is not ionized. As used herein, the term monobasic salt refers to the compounds of formulas (I) and (IV) wherein the phosphate (—O—P(=O)(O$^-$)$_2$ group is fully ionized. Illustrative embodiments of zwitterions of nicotinamide mononucleotide and the compound of formula (IV) are:

and

Examples of protonated salts of nicotinamide mononucleotide of formula (I) and the compound of formula (IV) include:

wherein X$^-$ can be any suitable monovalent anion.

Examples of a monobasic salt of nicotinamide mononucleotide of formula (I) and the compound of formula (IV) include:

wherein M$^+$ can be any suitable monovalent cation. In other embodiments, the monobasic salt can be associated with any suitable divalent cation M$^{2+}$, as illustrated for nicotinamide mononucleotide:

The salts can be prepared by reacting the zwitterionic forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. In embodiments, the protonated and monobasic salts comprise pharmaceutically acceptable salts. Preferred monobasic salts include sodium and potassium salts. Preferred protonated salts include hydrochloride and hydrobromide salts.

In embodiments, the protonated salt is produced during the conversion of compound 6 to compound 4. The protonated salt 7 and zwitterion 4 can be produced as shown in Scheme 2:

Reagents and conditions: (a) HCl/MeOH, pH=1-2; (b) aq. Na$_2$CO$_3$, pH=6-7

The following example further illustrates the invention but, of course, should not be construed as in any way limiting its scope.

EXAMPLE 1

This example demonstrates a process for the synthesis of nicotinamide mononucleotide riboside, in accordance with an embodiment of the invention.

Step 1: Preparation of 3-Carbamoyl-1-((3aR,4R,6R,6aR)-6-(hydroxymethyl)-2,2-dimethyltetrahydrofuro[3,4-d][1,3]dioxol-4-yl)pyridin-1-ium) (2)

In a flame dried flask under an argon atmosphere, concentrated sulfuric acid (22 µL, 0.40 mmol) was slowly added to dry acetonitrile (2.0 mL) at 0° C. After 5 minutes, 2,2-dimethoxypropane (0.6 mL, excess) was added to the stirred acetonitrile solution at the same temperature. Nicotinamide riboside solid (1) (250 mg, 0.61 mmol) was added to the reaction mixture at 0° C., and the reaction was immediately warmed to 25° C. over 10 min. The progress of the reaction was monitored by thin layer chromatography (TLC) and high performance liquid chromatography (HPLC). HPLC showed 95% of starting material was consumed after 10 min. The reaction mixture was cooled again to 0° C. in an ice bath, and was quenched by addition of powdered solid $Na_2CO_3$ (50 mg 0.47 mmol) and stirred for 5 min. 0.1 mL water was added slowly to improve neutralization of the acid. Residual solids were filtered, and the filtrate (acetonitrile) was evaporated under high vacuum to obtain the crude product. The crude product was dissolved in a minimum volume of DCM and was purified by silica gel column (60 A°) using DCM/MeOH (9:1) to obtain 2 as a white solid. Yield 96%.

$^1$H NMR (CD$_3$OD, 500 MHz): δ 9.56 (s, 1H, H-2), 9.31 (d, 1H, J=6.3 Hz, H-6), 9.02 (d, 1H, J=7.8 Hz, H-4), 8.25 (t, 1H, J=7.6 Hz, H-5), 6.41 (s, 1H, H-4'), 5.22-5.19 (m, 1H, H-1'), 4.99 (d, 1H, J=5.7 Hz, H-2'), 3.99-3.94 (dd, 1H, J=1.8 and 12.3, H-3'), 3.82-3.77 (dd, 1H, J=2.3 and 11.6 Hz, H-5'a), 3.70-3.68 (m, 1H, H-5'b), 1.66 (s, 3H, —CH$_3$), 1.45 (s, 3H, —CH$_3$). $^{13}$C NMR (CD$_3$OD, 125 MHz): 142.7, 142.4, 140.5, 133.8, 127.4, 114.0, 103.9, 90.4, 87.7, 82.3, 61.3, 34.0, 25.9, 23.9.

Step 2: Preparation of 3-Carbamoyl-1-((3aR,4R,6R,6aR)-2,2-dimethyl-6-((phosphonooxy)methyl)tetrahydrofuro[3,4-d][1,3]dioxol-4-yl)pyridin-1-ium) (3)

phosphate solution. The mixture was stirred at 0° C. for 48 hours. Progress of the reaction was monitored by HPLC, which showed that 75% of starting material was consumed after 48 h, with concomitant increase in product 3 which eluted at a shorter retention time. The reaction mixture was cooled to 0° C. and was quenched with 3 consecutive 1 mL portions of cold saturated $Na_2CO_3$ solution until the acid was neutralized and bubbling ceased. Triethyl phosphate was removed by extraction with ethyl acetate (3×10 mL). The combined ethyl acetate layers were then extracted with water (3×5 mL) to remove the crude product. The combined water layers and initial water layer containing product 3 were dried under high vacuum to obtain the crude product. The crude product was dissolved in a minimum volume of 9:1 DCM:methanol as needed to solubilize, and the crude product was purified by column chromatography on silica gel using DCM/MeOH (6:4) to provide (3) as a white solid. Yield 80%.

$^1$H NMR (D$_2$O, 500 MHz): δ 9.31 (s, 1H, H-2), 9.11 (d, 1H, J=6.4 Hz, H-6), 8.86 (d, 1H, J=8.2 Hz, H-4), 8.22-8.18 (m, 1H, H-5), 6.37 (d, 1H, J=2.5 Hz, H-4'), 5.30 (dd, 1H, J=2.6 and 5.8 Hz, H-1'), 5.07 (d, 1H, J=5.7 Hz, H-2'), 4.99-4.97 (m, 1H, H-3'), 4.18 (t, 1H, J=2.1 Hz, H-5'a), 4.16 (t, 1H, J=2.1 Hz, H-5'b), 1.60 (s, 3H, —CH$_3$), 1.41 (s, 3H, —CH$_3$). $^{13}$C NMR (D$_2$O, 125 MHz): 150.8, 145.7, 139.5, 128.2, 103.2, 88.2, 86.8, 82.4, 65.2, 30.0, 25.9, 24.2.

Step 3: Preparation of 3-Carbamoyl-1-((2R,5R)-3,4-dihydroxy-5-((phosphonooxy)methyl)tetrahydrofuran-2-yl)pyridin-1-ium) (4)

Compound 2 (880 mg, 2 mmol) was added to 8 mL of dry triethyl phosphate at 0° C. under an argon atmosphere in a flame-dried flask. After 10 minutes, 470 μL, phosphorous oxychloride (2.5 eq, 5 mmol) was slowly added portion-wise (176 μL+176 μL+118 μL) to the stirred and chilled triethyl (A) Deprotection in Dichloromethane/Water:
TFA (0.6 mL, 7.8. mmol) was slowly added to a solution of compound 3 (1000 mg, 2.67 mmol) in 30 mL dichloromethane and water (1:1) at 0° C. The reaction mixture was stirred vigorously and allowed to warm to room temperature. After 16 hours (reaction progress was monitored by HPLC, which showed that 95% of starting material was consumed after 16 h), the reaction mixture was evaporated. Residual water was neutralized with minimal Na$_2$CO$_3$ to pH 6, and the water layer was evaporated to obtain the crude product. The crude product was dissolved in minimum water and was purified by a C18 column using water to provide NMN (4) as a white solid. Yield 90%.

$^1$H NMR (D$_2$O, 500 MHz): δ 9.39 (s, 1H, H-2), 9.21 (d, 1H, J=6.2 Hz, H-6), 8.90 (d, 1H, J=8.1 Hz, H-4), 8.22 (t, 1H, J=6.9 Hz, H-5), 6.14 (d, 1H, J=5.6 Hz, H-4'), 4.56 (t, 1H, J=2.4 Hz, H-1'), 4.48 (t, 1H, J=5.3 Hz, H-2'), 4.38-4.35 (m, 1H, H-3'), 4.25-4.20 (m, 1H, H-5'a); 4.01-4.05 (m, 1H, H-5'b). $^{13}$C NMR (D$_2$O, 125 MHz): 165.9, 146.0, 142.5, 139.9, 134.0, 128.5, 100.0, 87.5, 77.8, 75.1, 64.2.

(B) Deprotection in Methanolic HCl:

Concentrated hydrochloric acid (672 µL, 8.06 mmol) was slowly added to a solution of compound 3 (1000 mg, 2.67 mmol) in 30 mL of methanol under an argon atmosphere in a flame dried flask. The reaction mixture was allowed to warm to room temperature. After 40 hours HPLC showed no starting material remained. The reaction mixture was then evaporated to dryness, and 5 mL water was added to dissolve solids. Solid Na$_2$CO$_3$ was added to adjust pH to 5. NMN was purified on a C18 column using water as eluent to provide NMN (4) as a white solid. Yield 67%.

$^1$H NMR (D$_2$O, 500 MHz): δ 9.39 (s, 1H, H-2), 9.21 (d, 1H, J=6.2 Hz, H-6), 8.90 (d, 1H, J=8.1 Hz, H-4), 8.22 (t, 1H, J=6.9 Hz, H-5), 6.14 (d, 1H, J=5.6 Hz, H-4'), 4.56 (t, 1H, J=2.4 Hz, H-1'), 4.48 (t, 1H, J=5.3 Hz, H-2'), 4.38-4.35 (m, 1H, H-3'), 4.25-4.20 (m, 1H, H-5'a); 4.01-4.05 (m, 1H, H-5'b). $^{13}$C NMR (D$_2$O, 125 MHz): 165.9, 146.0, 142.5, 139.9, 134.0, 128.5, 100.0, 87.5, 77.8, 75.1, 64.2.

EXAMPLE 2

This example demonstrates the titration of nicotinamide mononucleotide chloride salt with sodium hydroxide.

Figure 1:
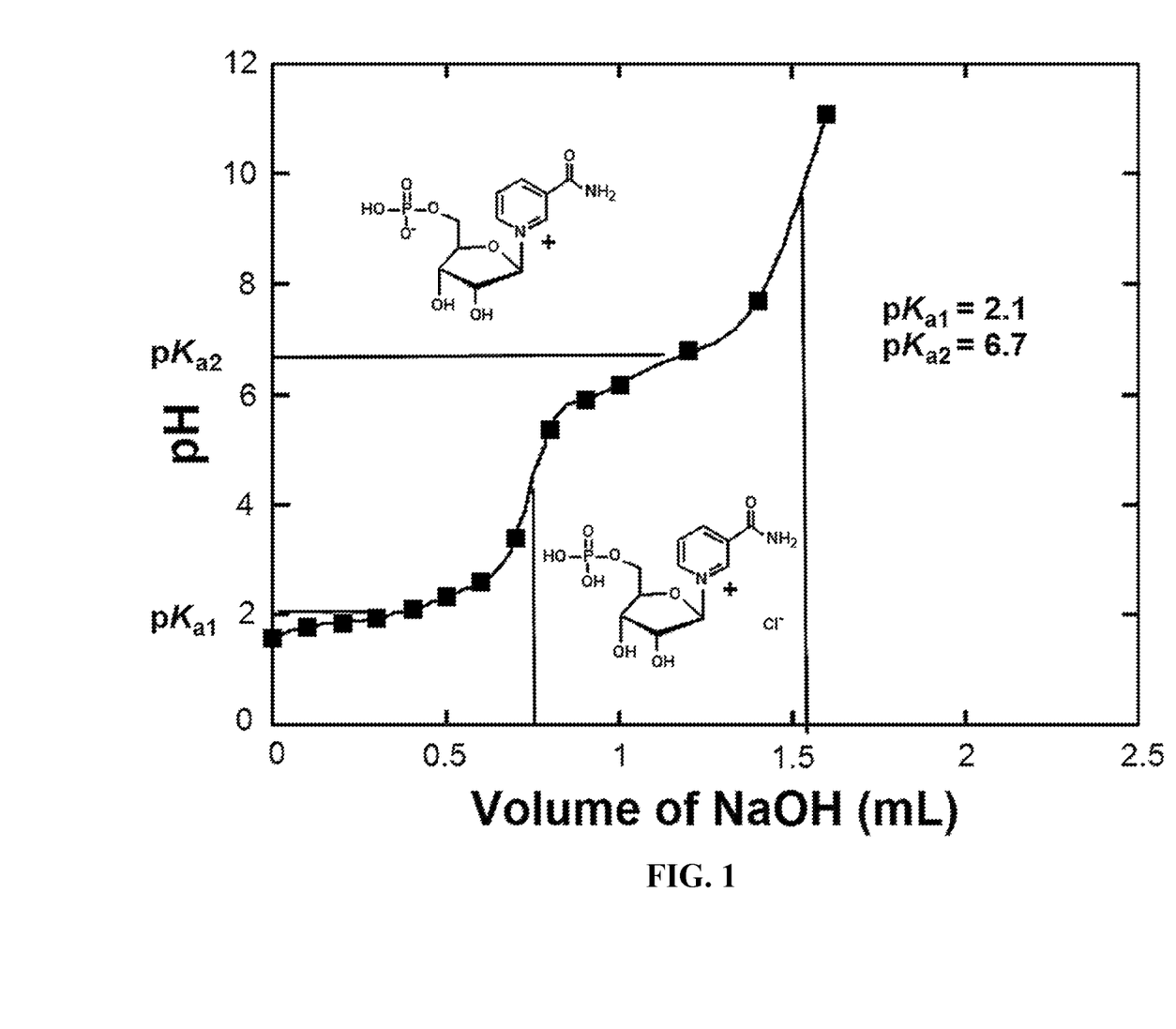
FIG. 1 shows a titration curve for nicotinamide mononucleotide chloride.

Nicotinamide mononucleotide-chloride salt (110 mg, 0.29 mmol) was dissolved in 2 ml water (approximate concentration 150 mM). To the resulting solution 200 µL of 150 mM NaOH solution (0.1 eq) was added and pH was measured by pH meter. Addition of 200 µL of 150 mM NaOH solution was continued and the pH measured and plotted. 2 pKa values were determined by this titration, namely the first pK$_{a1}$=2.1 for the conversion of [NMNH]Cl to the neutral zwitterion form and then pK$_{a2}$=6.7 to form the mono anion [NMN]$^-$ (Scheme 3). The titration of both protons indicates the successful stabilization and characterization of the cation [NMNH]Cl form of NMN.

Scheme 3

The titration curve is shown in FIG. 1.

EXAMPLE 3

This example shows the $^1$H NMR and $^{31}$P NMR spectra of zwitterion 4 and chloride salt 7.

Figure 2:
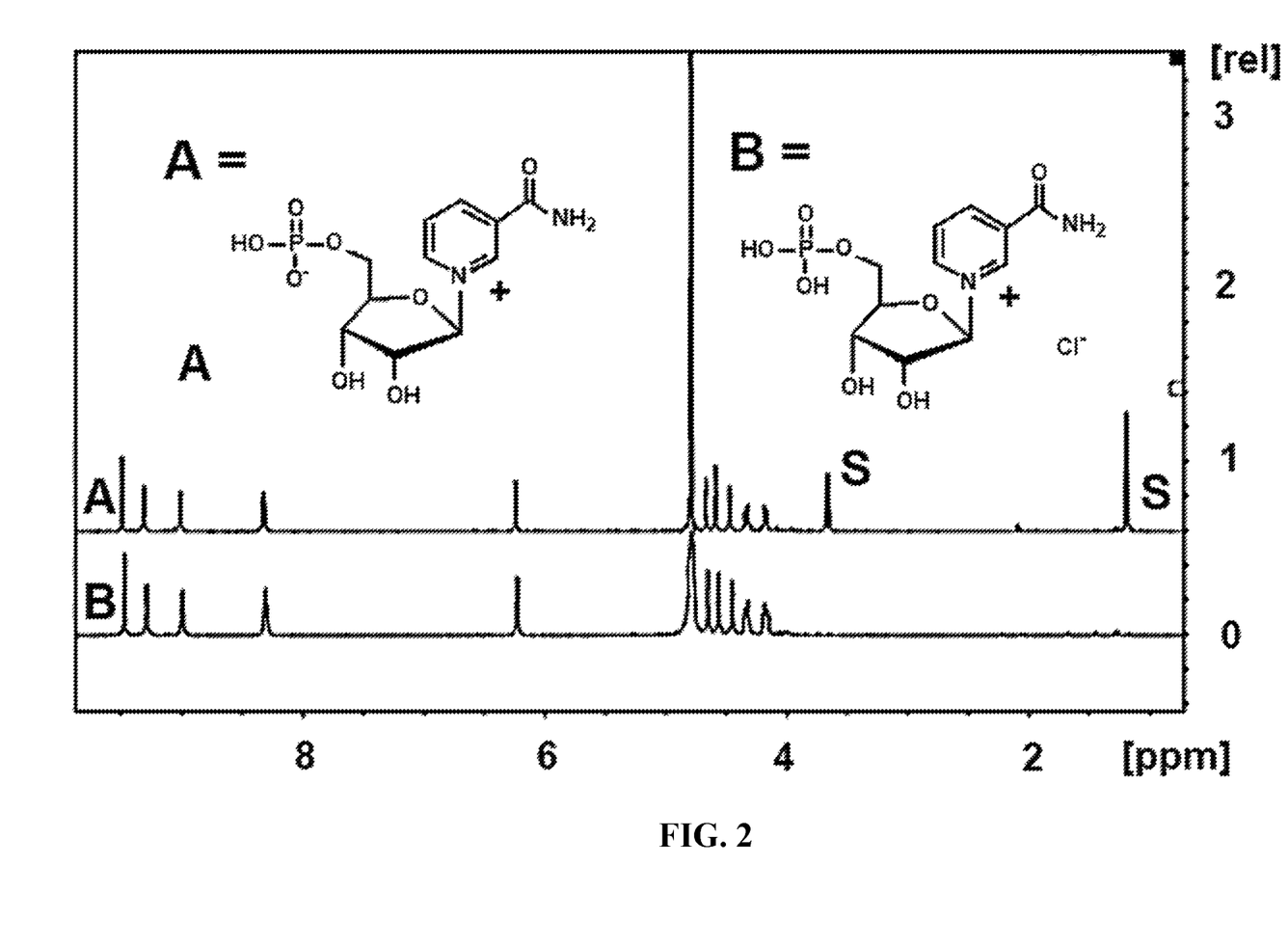
FIG. 2 shows the 500 MHz ¹H NMR (500 MHz, $D_2O$) spectra of zwitterion 4 and chloride salt 7 in $D_2O$ superimposed. The peaks labeled "S" for the zwitterions are due to ethanol impurity.

FIG. 2 shows the 500 MHz $^1$H NMR (500 MHz, D$_2$O) spectra of zwitterion 4 and chloride salt 7 in D$_2$O superimposed.

Figure 3:
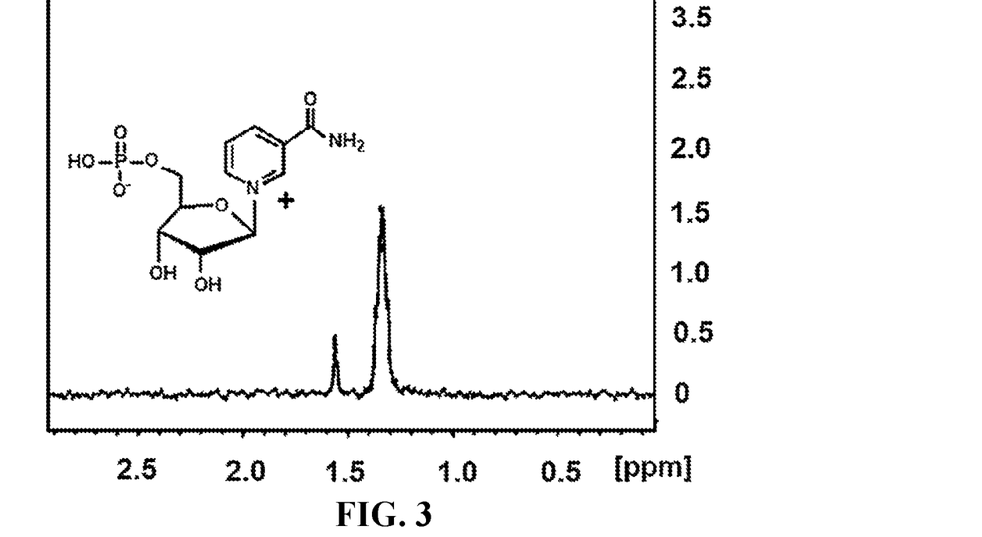
FIG. 3 shows the ³¹P NMR (500 MHz, $D_2O$) spectrum of zwitterion 4.

FIG. 3 shows the $^{31}$P NMR 500 MHz, D$_2$O) spectrum of zwitterion 4.

Figure 4:
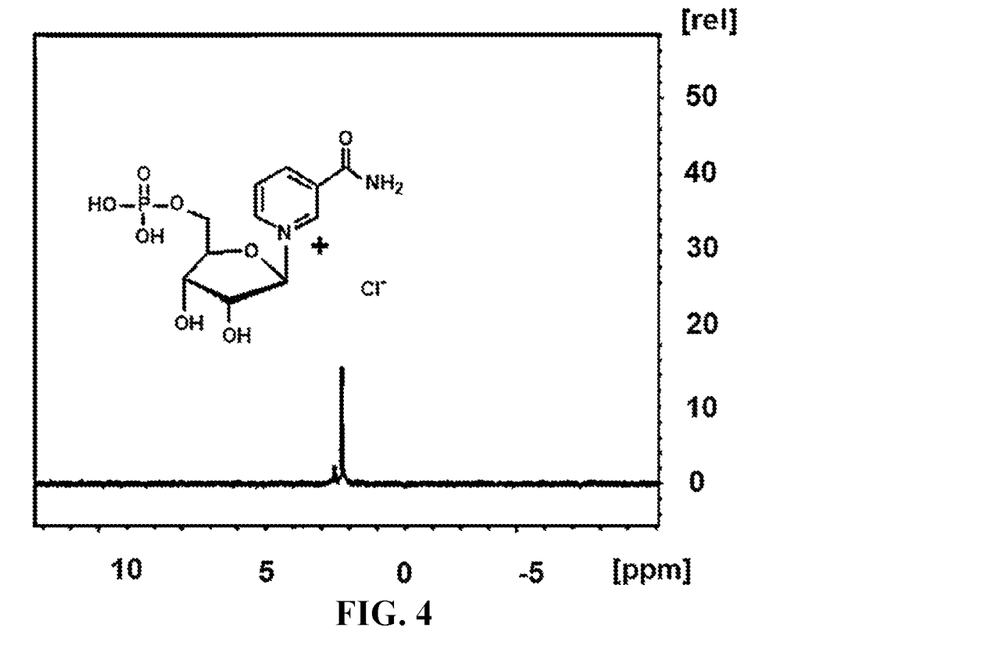
FIG. 4 shows the ³¹P NMR (500 MHz, $D_2O$) spectrum of chloride salt 7.

FIG. 4 shows shows the $^{31}$P NMR 500 MHz, D$_2$O) spectrum of chloride salt 7.

Figure 5:
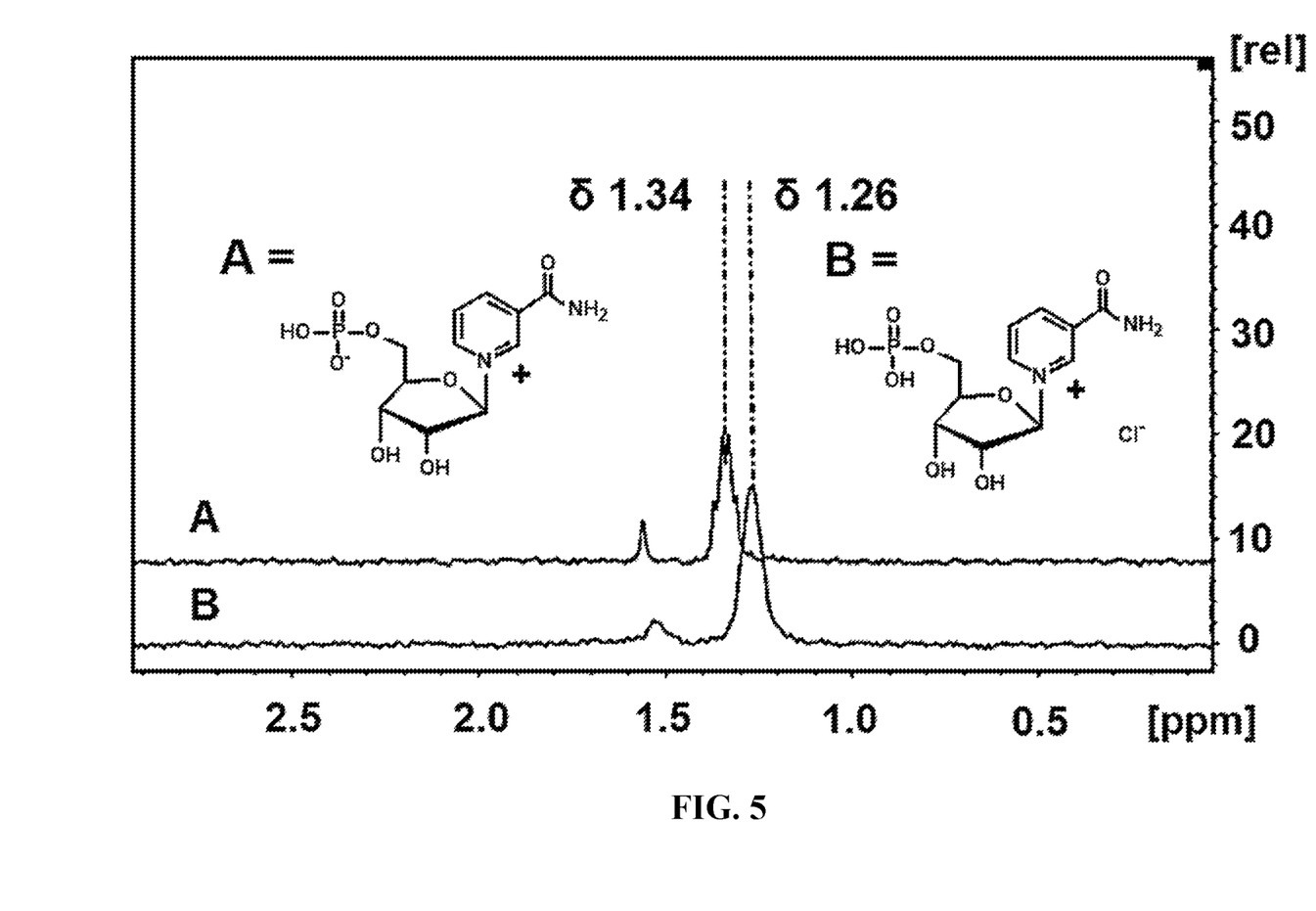
FIG. 5 shows the overlaid ³¹P NMR spectra of zwitterion 4 and chloride salt 7.

FIG. 5 shows the overlaid $^{31}$P NMR spectra of zwitterion 4 and chloride salt 7.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods

The invention claimed is:

1. A process for the preparation of nicotinamide mononucleotide having formula (I):

(I)

or a salt thereof, wherein the process comprises the step of reacting a compound of formula (IV):

(IV)

wherein $R^1$ and $R^2$ are independently $C_1$-$C_6$ alkyl or, taken together along with the carbon atom to which they are attached, form a 5-7 membered carbocyclic ring,
with an acid catalyst in a mixture of solvents to provide nicotinamide mononucleotide,
wherein the acid catalyst is trifluoroacetic acid, and
wherein the mixture of solvents is a mixture of dichloromethane and water.

2. The process of claim 1, wherein the reaction is carried out at a temperature of from about 0° C. to about room temperature.

3. A process for the preparation of nicotinamide mononucleotide having formula (I):

(I)

or a salt thereof, wherein the process comprises the step of reacting a compound of formula (IV):

(IV)

wherein $R^1$ and $R^2$ are independently $C_1$-$C_6$ alkyl or, taken together along with the carbon atom to which they are attached, form a 5-7 membered carbocyclic ring,
with an acid catalyst in a solvent to provide nicotinamide mononucleotide,
wherein the solvent is methanol, and
wherein the acid catalyst is concentrated hydrochloric acid present in an amount of about 3% (volume/volume) relative to a volume of methanol.

4. The process of claim 3, wherein the reaction is carried out at a temperature of from about 0° C. to about room temperature.

5. The process of claim 3, wherein the reaction is carried out over a time period of about 40 hours or more.

* * * * *

UNITED STATES PATENT AND TRADEMARK OFFICE
CERTIFICATE OF CORRECTION

PATENT NO. : 11,028,118 B2
APPLICATION NO. : 16/820548
DATED : June 8, 2021
INVENTOR(S) : Anthony Sauve et al.

Page 1 of 1

It is certified that error appears in the above-identified patent and that said Letters Patent is hereby corrected as shown below:

On the Title Page

At (72) Inventors, "Farheen Sultana Yang Mohammed" should read --Farheen Sultana Mohammed--.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*